(12) United States Patent
Virtanen

(10) Patent No.: US 6,402,919 B1
(45) Date of Patent: Jun. 11, 2002

(54) CAPILLARY ELECTROPHORESIS APPARATUS

(75) Inventor: Rauno Virtanen, Espoo (FI)

(73) Assignee: Valtion Teknillinen Tutkimuskeskus (FI)

( * ) Notice: Subject to any disclaimer, the term of this patent is extended or adjusted under 35 U.S.C. 154(b) by 0 days.

(21) Appl. No.: 09/509,646

(22) PCT Filed: Sep. 30, 1998

(86) PCT No.: PCT/FI98/00773

§ 371 (c)(1),
(2), (4) Date: May 25, 2000

(87) PCT Pub. No.: WO99/17111

PCT Pub. Date: Apr. 8, 1999

(30) Foreign Application Priority Data

Oct. 1, 1997 (FI) ................................. 973854

(51) Int. Cl.$^7$ ............................... G01N 27/26
(52) U.S. Cl. ....................... 204/604; 204/601
(58) Field of Search ............... 204/601, 604, 204/451, 453

(56) References Cited

FOREIGN PATENT DOCUMENTS

| EP | 0 497 488 A2 | 8/1992 |
|---|---|---|
| WO | WO 95/33989 | 12/1995 |
| WO | WO 97/33166 | 9/1997 |

*Primary Examiner*—Jill Warden
*Assistant Examiner*—Alex Noguerola
(74) *Attorney, Agent, or Firm*—Merchant & Gould P.C.

(57) ABSTRACT

The invention relates to a capillary electrophoresis apparatus, comprising background solution containing reservoirs, which are interconnected by way of a separating capillary (1), current electrodes (E) connected to a voltage source, and a detector (4) essentially in the proximity of the outlet end of the separating capillary (1), as well as one or more solution reservoirs (R1–R3) on the injection side of the apparatus and one or more solution reservoirs (R4–R6) on the detector side of the apparatus, the ends of the separating capillary (1) being placed in expansions (5, 7), intended for feeding various solutions from the reservoirs (R1–R6) and extending from the bottom ends of capillary tubes (2, 3), said expansions extending as waste ducts (W1, W2) to waste containers, said waste containers being located at a distance from the ends of the separating capillary (1), and the current electrodes (E) being located in the waste ducts (W1, W2), preferably in the proximity of the discharge ends thereof.

10 Claims, 2 Drawing Sheets

CAPILLARY ELECTROPHORESIS APPARATUS

The present invention relates to a capillary electrophoresis apparatus, suitable for readily performing a variety of capillary electrophoresis processes, such as zone electrophoresis, isoelectric focusing, and electrokinetic micelle-chromatography.

FIELD OF THE INVENTION

Electrophoresis is an electrochemical process, which can be used for separating from each other electrically charged and, with certain special techniques, also uncharged particles, present in an electrolytic solution and having a size which ranges from the smallest ions and molecules to colloidal particles. Depending on the electrical charge and other properties thereof, the particles travel at different speeds in an electrical field. There are several ways of classifying electrophoretic process. One classification is based on a carrier or an apparatus used for eliminating convection in a liquid phase, e.g. a paper, a gel, a column, or a capillary.

BACKGROUND OF THE INVENTION

Capillary electrophoresis is one of the most rapidly advancing applications of analytic chemistry. In the process, a background solution is contained in such a thin tube, a capillary, that the viscous forces of a liquid preclude convection. The inner diameter of a capillary is usually within the range of 0.01 to 1 mm. Electrophoresis is hence carried out in a free solution for eliminating disturbances caused by a carrier. It is also easy to free a capillary of thermal energy evolved by an electric current, thus enabling the use of a high electric field for a more expeditious separation. In addition, capillary electrophoresis can be readily automated.

In capillary electrophoresis, two vessels containing a electrolytic background solution are interconnected by means of a capillary tube which contains the same solution. Each vessel is provided with an electrode. A sample to be investigated is placed in the inlet end of the capillary as a short zone. Generally, in order to supply a sample, the end of a capillary is moved from the background solution vessel to the sample vessel and back. This operation causes disturbances and distortions in the background solution at the end of a capillary and in the sample zone and leads to an impaired accuracy of the method. It is also inevitable that the current be switched off for the duration of moving the capillary from one vessel to the other, which may cause fluctuations in running conditions. The same drawbacks result also from replacing the background solution during the course of a run.

Reactions occurring on the electrodes also change the composition of a solution contained in the background solution vessels and these changes may propagate into the capillary to cause distortion in the parameters of a test series.

Capillary electrophoresis can be performed by using various applications. The most commonly used applications are capillary zone electrophoresis (CZE), capillary isoelectric focusing (CIEF), capillary isotachophoresis (CITP), and micellar electrokinetic capillary chromatography (MECC). Although different in appearance, these applications are controlled by the same electrochemical laws. Various applications are created by applying various initial and boundary conditions to an electrophoresis system.

The commercially available capillary electrophoresis devices usually allow various electrophoresis applications to be performed. However, such devices are hampered by certain drawbacks or structural features, which limit the easy transition from one application to another and also the changing of system parameters during a run.

Several researchers have introduced technical solutions, capable of partially eliminating the above drawbacks. Virtanen, Acta Polytechnica Scandinavica, Chemistry Including Metallurgy Series, No. 123 (1974), pp. 1–67, employed, as early as in the 1960's, injection technology which allows the injection of a sample while electric current is on Verheggen et al., J. Chromatogr., 452 (1988), pp. 615–622, and Zare et al., U.S. Pat. No. 5,141,621, have also introduced a method for injecting a sample into a capillary electrophoresis apparatus without switching off electric current. However, these methods and apparatus do not provide means for exploiting the multitude of possibilities offered by the theoretical similarity of various electrophoresis applications.

SUMMARY OF THE INVENTION

An object of the present invention is to provide a novel capillary electrophoresis apparatus, which is capable of eliminating the above drawbacks and which enables easy performance of all various applications of capillary electrophoresis with one and the same apparatus. In order to achieve this, the invention is characterized by what is set forth in the characterizing clause of claim 1.

In order to perform a given electrophoresis application, it is necessary to choose certain initial and boundary conditions. The regulation of boundary conditions in a capillary electrophoresis system means that the composition of a background solution present in the proximity of the ends of a capillary must be controlled. According to the invention, this is performed by continuously pumping fresh solution past the ends of a separating capillary. This also prevents reaction products resulting from electrode reactions from passing into the capillary. In order to avoid the high consumption of a background solution, the solution channels must have as small a volume as possible. The design or an apparatus according to the present invention is based on this principle. In the apparatus of the invention, the test conditions can be chosen without restrictions and modified arbitrarily during a run.

BRIEF DESCRIPTION OF THE DRAWINGS

The invention will now be described in detail with reference made to the accompanying drawings, in which.

DETAILED DESCRIPTION OF THE INVENTION

Figure 1:
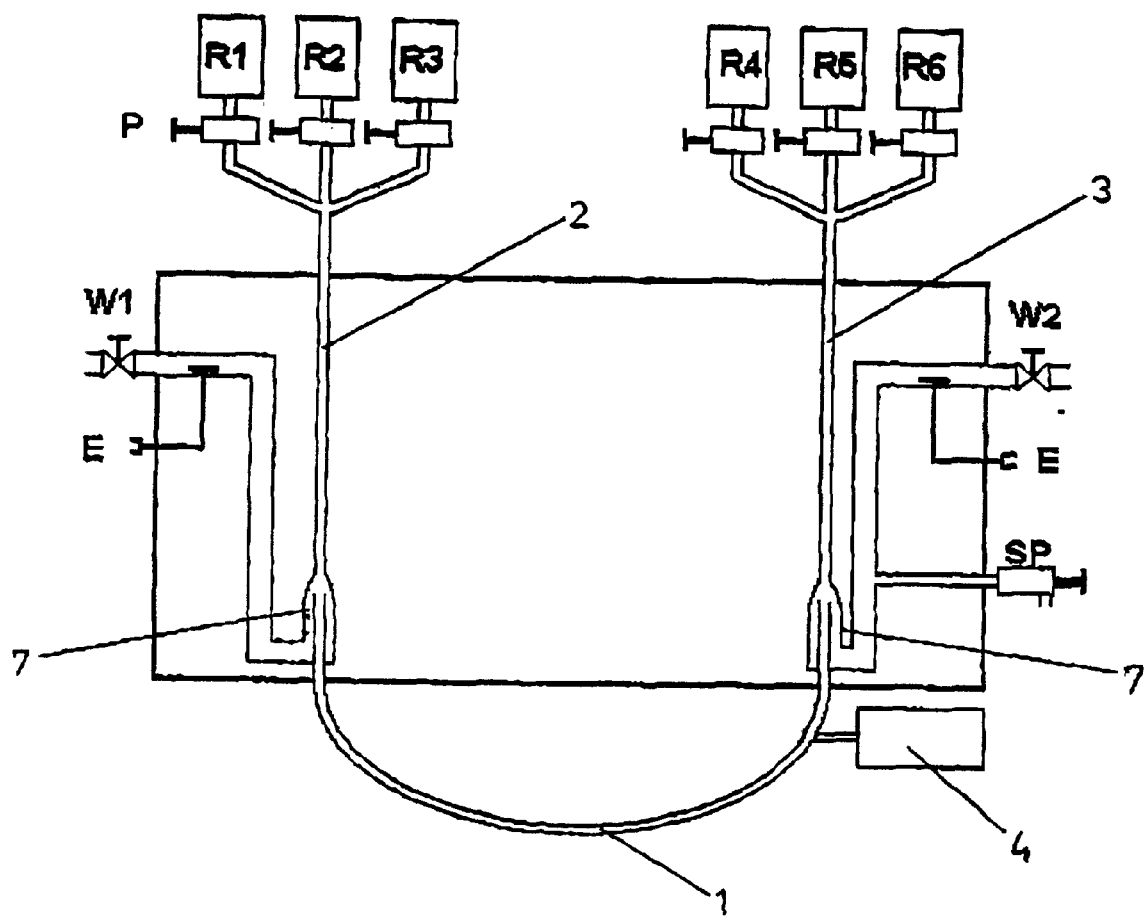
FIG. 1 shows one embodiment of the invention.
Figure 2:
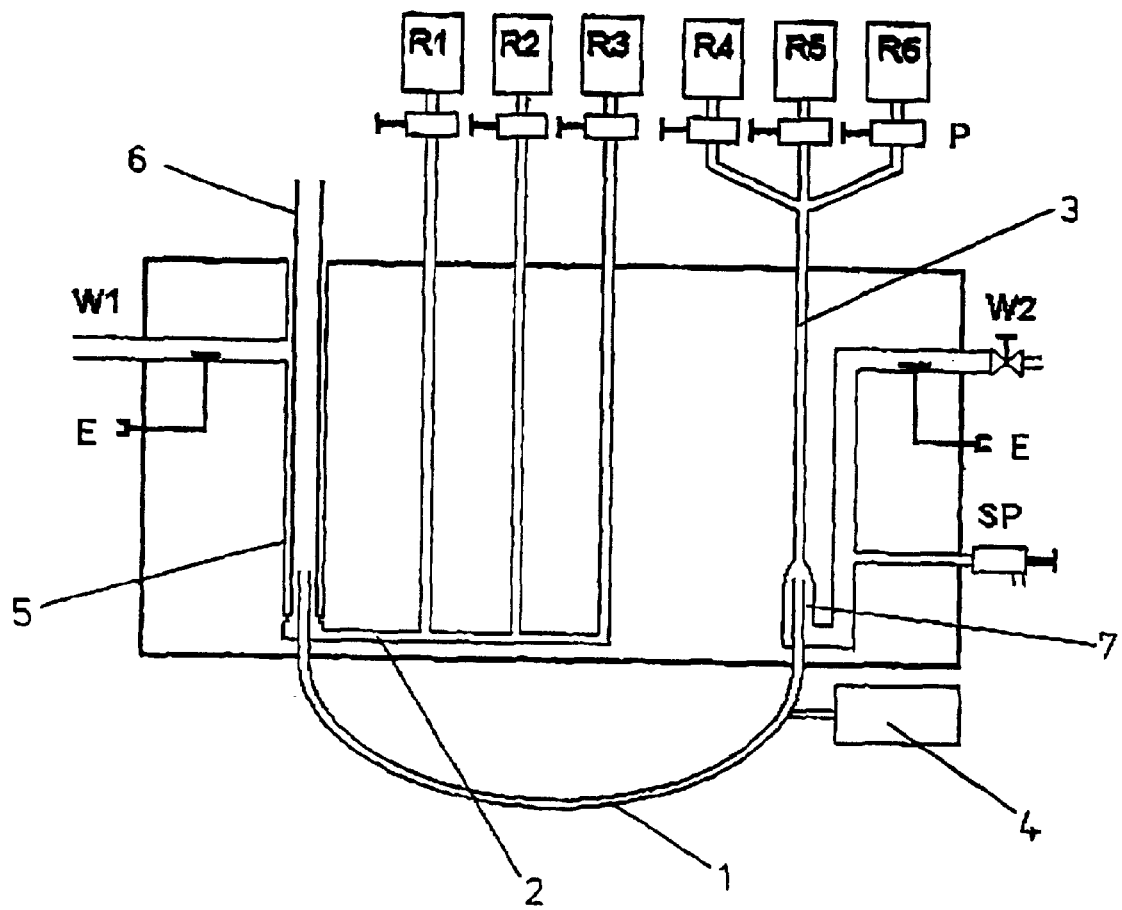
FIG. 2 shows another embodiment of the invention.

FIGS. 1 and 2 depict an apparatus of the invention, wherein the ends of a separating capillary 1 are accommodated in expansions 7 and 5 (FIG. 2), intended for feeding various solutions from reservoirs R1–R6 and extending from the bottom ends of capillary tubes 2 and 3. The expansions have a diameter which is preferably about 0.5–3 mm. These expansions extend to waste containers in the form of waste ducts W1 and W2 having a width equal to the expansion. The capillary tubes 2 and 3 have and inner diameter which preferably 0.01–1.0 mm, and more preferably 0.02–0.5 mm. The arrangement of the capillary tubes 2 and 3 can also be different from what is depicted in the figures. The electrolytic solution used as a background solution flows from any of the reservoirs R1–R3 and from any of the reservoirs R4–R6 along these capillary tubes 2 and 3 slowly past both ends of the separating capillary 1 towards current electrodes E, present in the waste ducts W1 and W2 and connected to a voltage source, and finally discharges from the system along the waste ducts into the waste containers. The waste containers are located at a distance from the ends of the separating capillary 1 and the electrodes E are preferably located in the outlet ends of the waste ducts W1 and W2, the migration of electrolysis products formed on the electrodes into the separating capillary being precluded e.g. by virtue of a long and spacious waste duct. The flow rate is adjusted to uphold the required conditions in the separating capillary 1 and, furthermore, to deny the electrolysis products of the electrodes an access to the separating capillary.

The feed solution coming from the solution reservoirs R1–R6 can be replaced independently by means of pumps P, and the flow rate of various feed solutions can also be controlled independently. After completing an electrophoresis run, washing and balancing solutions present in any of the reservoirs R1–R6 can be pumped through the capillary system. The pump can also be fitted in the waste duct W2, in which case it operates on a suction principle. Thus, in FIGS. 1 and 2, the pumps P can be replaced with valves and suction is produced by means of a pump SP. The number of pumps and valves is optional and can be selected according to a present application. In case the flow rate does not require a high accuracy, it is also possible to replace the pumps entirely with valves and to create a flow by means of gravity or by means of a negative pressure or positive pressure existing in the solution containers R1–R6.

Essentially in the proximity of the discharge end of the separating capillary 1 is mounted a detector 4, by means of which particles separated in the capillary are detected. The detection can be effected e.g. on the basis of the absorbancy of a sample. Operation of the entire apparatus can be controlled by means of a micro-processor.

By using appropriate pumps and valves, it is possible to perform a closed or open capillary electrophoresis or to establish a precalculated flow rate in a capillary. The apparatus of the invention can also be used for running various chemical gradients and pulses during a run from either end of a separating capillary.

In the apparatus of the invention, a sample can be injected basically at least in two different ways. First of all, one of the solution reservoirs R1–R3 present on the injection side of the apparatus shown in FIGS. 1 and 2 may contain a sample solution. Thus, the sample is delivered along the capillary 2 into the separating capillary 1.

The principle of another sample feeding method is depicted in FIG. 2. This method of sample feeding is also described in the Applicant's earlier FI Patent application 961069, incorporated here as a reference. In this embodiment for an apparatus of the invention, on the injection side of the apparatus, the end of a separating capillary 1 is accommodated in an open-top tube 5, which constitutes an expansion, extending from the bottom end of the above mentioned capillary tube 2 corresponding to the expansion 7 of FIG. 1, and which has an inner diameter exceeding the outer diameter of the separating capillary. The tube 5 also functions as a section of the waste duct W1. The background solution flows to the proximity of the end of the separating capillary 1 essentially from the bottom area of the tube 5 along the capillary 2. In this mode of delivering a sample, the sample solution is carried to the proximity of the end of the separating capillary 1 by means of a movable sample feeding capillary 6, having an inner diameter, preferably about 0.5–1.5 mm, which exceeds the outer diameter of the end of the separating capillary 1 of a capillary electrophoresis apparatus. The difference between the inner diameter of the sample feeding capillary 6 and the outer diameter of the separating capillary 1 is typically about 0.2–5 mm. The sample feeding capillary 6 is filled with a sample solution and its end is placed around the end of the separating capillary 1 in a telescopic manner. The sample solution contained in the sample feeding capillary surrounds the end of the separating capillary completely, the background solution being totally replaced by the sample solution around the end of the separating capillary 1. The electrically charged particles present in the sample travel into the separating capillary 1 through the action of an electric current. The electro-osmotic flow of the solution carries the sample solution into the separating capillary 1. It is also possible to use a suction pump SP in the injection of a sample. The sample is fed for a certain length of time, whereafter the sample feeding capillary 6 is withdrawn from around the inlet end of the separating capillary 1.

In the assembly of FIG. 2, a sample can also be fed without using a separate sample feeding capillary 6, the sample solution being supplied from any of the reservoirs R1–R3 along the capillary 2.

If a sample solution is fed by pumping while the electric field is switched on, a controllable amount of sample migrates into the separating capillary 1. The amount of a sample to be injected is determined by controlling the pumping time, electric field, and electro-osmotic flow rate.

The electro-osmotic and hydrodynamic net flow in the separating capillary can be eliminated by closing the channel system on the side of a detector 4. In this case, the feeding can be effected purely electrokinetically. By modifying various parameters, type of injection, electric field, and solution flow, it is readily possible with the apparatus of the invention to introduce many different ways of sample feeding.

If desirable, it is possible to select any application and running conditions at all and to modify those during a run.

By using an apparatus of the invention, it is easy to select and implement initial and boundary conditions for various electrophoresis applications. In addition, it is possible to use combined methods by modifying the boundary conditions during an electrophoresis run. The following describes a few examples of versatile application possibilities for an apparatus of the invention.

EXAMPLE 1

In reference to FIG. 2, there is described a simple zone electrophoresis application for an apparatus of the invention. The injection side only requires a single pump for feeding a background solution from a background solution reservoir (e.g. reservoir R1). The detector side requires a pump for feeding a background solution (e.g. from reservoir R4) and furthermore, if desired, pumps for washing and stabilizing solutions (e.g. reservoirs R5 and R6). The suction pump SP is not necessary. The pumping of background solution is continued past both ends of the separating capillary 1. The voltage is upheld all the time. Both waste ducts W1 and W2 are kept open to ambient pressure, the hydrostatic pressure difference in the separating capillary being thereby zero and the electro-osmotic flow proceeding freely. As soon as the running conditions have stabilized, a sample is injected by placing the sample feeding capillary 6 containing a sample solution around the end of the separating capillary 1 in the tube 5. The sampling capillary is withdrawn after an appropriate length of time and the separating run begins. When the run is completed, the separating capillary 1 is prepared for the next sample injection. This can be performed in a variety of ways, as the case may be. If washing is not necessary, it is possible to wait until the electric current and electro-osmotic flow restore the background solution in the separating capillary. The restoration can be effected quickly by closing the waste duct valve, such that the flow of background solution is deflected to run through the separating capillary 1. As soon as the conditions have restabilized, the apparatus is ready for another sample injection.

It is possible to keep the waste duct W2 closed on the detector side during a run. This is called a closed capillary application. Hence, the pumping must also be stopped on the detector side, unless it is desired to cause a laminar hydrodynamic flow in the separating capillary 1. Even though the pumping is stopped, the migration of electrolysis products forming on the electrodes E into the separating capillary 1 will be precluded because of a long and spacious waste duct. In this case, there will be no electro-osmotic net flow, which may cause e.g. fluctuation in running times.

EXAMPLE 2

A second application described here is isoelectric focusing. It is carried out with the apparatus of FIG. 1. In this application, the injection side is provided with three pumps (reservoirs R1, R2, and R3) and the detector side with two pumps (e.g. reservoirs R4 and R5). The suction pump SP is not necessary. After the initial filling and stabilization of the capillary system, the procedure is as follows. The separating capillary is filled with an ampholyte solution by closing the waste duct W1. The waste duct W2 is open. Ampholyte solution is pumped from the reservoir R2. Sample solution is pumped from the reservoir R3, followed by pumping from the reservoir R2 still a short plug of ampholyte solution. The sample can also be mixed beforehand with the ampholyte solution, which may fill the entire capillary system. The system is prepared for focusing by opening the waste duct W1 and by pumping anolyte $H_3PO_4$ from the reservoir R1 and catholyte NaOH from the reservoir R4 past the ends of the separating capillary into the waste ducts. A current is switched on and focusing begins. After the focusing is completed, the solution present in the separating capillary is forced slowly past the detector 4 by closing the waste duct W1 and by continuing pumping from the reservoirs R1 and R4. Preparation of the capillary system for another run may include washing with NaOH from the reservoir R4 and with water from the reservoir R5, when the waste duct W2 is closed and the waste duct W1 is open.

Described above are a few embodiments of the invention. Naturally, the invention is not limited to the described examples, as the principle of the invention can be modified within the scope of protection defined in the claims.

What is claimed is:

1. A capillary electrophoresis apparatus comprising background-solution containing reservoirs, which are interconnected by way of a separating capillary (1), current electrodes (E) connected to a voltage source, and a detector (4) essentially in the proximity of the outlet end of the separating capillary (1), further comprising one or more solution reservoirs (R1–R3) on an injection side of the apparatus and one or more solution reservoirs (R4–R6) on a detector side of the apparatus, and that the ends of the separating capillary (1) are operatively connected and placed in expansions (5, 7), the expansions (5, 7) intended for feeding various solutions from the reservoirs (R1–R6) and extending from the bottom ends of capillary tubes (2, 3), the capillary tubes (2, 3) deliver solution from the solution reservoirs (R1–R6) to said separating capillary (1), said expansions extending past ends of the separating capillary (1) toward waste ducts (W1, W2) to waste containers, said waste containers being located at a distance from the ends of the separating capillary (1), and that the current electrodes (E) are located in the waste ducts (W1, W2) in the proximity of discharge ends thereof.

2. A capillary electrophoresis apparatus as set forth in claim 1, wherein the expansions (5, 7) having a diameter of about 1–10 mm.

3. A capillary electrophoresis apparatus as set forth in claim 1, wherein the capillary tubes (2, 3) and the separating capillary (1) having an inner diameter of 0.01–1.0 mm.

4. A capillary electrophoresis apparatus as set forth in claim 3, wherein the capillary tubes (2, 3) and the separating capillary (1) having an inner diameter of 0.02–0.5 mm.

5. A capillary electrophoresis apparatus as set forth in claim 1, further comprising pumps (F) operatively connected with the solution reservoirs (R1–R6), the pumps (P) independently select a feed solution coming from the solution reservoirs (R1–R6) and control a flow rate of the feed solution.

6. A capillary electrophoresis apparatus as set forth in claim 1, characterized in that it comprises a suction pump (SP) in the waste duct W2 and valves and/or pumps (P) in conjunction with the solution reservoirs (R1–R6).

7. A capillary electrophoresis apparatus as set forth in claim 1, wherein the capillary tubes (2, 3) including a flow created by means of gravity or by means of negative pressure or positive pressure existing in the solution containers (R1–R6).

8. A capillary electrophoresis apparatus as set forth in claim 1, characterized in that, on the injection side of the apparatus, the apparatus includes an open-top tube (5) constituting an expansion extending from the bottom end of the capillary tube (2) for accommodating the end of the separating capillary (1).

9. A capillary electrophoresis apparatus as set forth in claim 8, characterized in that it includes a sample feeding capillary (6), having an inner diameter which exceeds the outer diameter of the end of the separating capillary (1) of the capillary electrophoresis apparatus and having an outer diameter which is smaller than the inner diameter of the tube (5) and by means of which the sample solution is brought to the proximity of the end of the separating capillary (1) inside the tube (5) in such a manner that the end of the sample feeding capillary (6) is located around the end of the separating capillary (1).

10. A capillary electrophoresis apparatus as set forth in claim 9, wherein the sample feeding capillary (6) having an inner diameter of about 0.5–1.5 mm.

* * * * *